United States Patent [19]

Sengbusch

[11] Patent Number: 4,702,841

[45] Date of Patent: Oct. 27, 1987

[54] METHOD OF AND ARRANGEMENT FOR EXTRACORPORAL REMOVAL OF TOXINS FROM BLOOD

[75] Inventor: Günter V. Sengbusch, Wuppertal, Fed. Rep. of Germany

[73] Assignee: Akzo NV, Arnhem, Netherlands

[21] Appl. No.: 443,738

[22] Filed: Nov. 22, 1982

[30] Foreign Application Priority Data

Nov. 30, 1981 [DE] Fed. Rep. of Germany ....... 3147377

[51] Int. Cl.$^4$ ............................................. B01D 13/00
[52] U.S. Cl. ................................... 210/638; 210/651; 210/259; 210/434
[58] Field of Search ............... 210/321.3, 321.1, 433.2, 210/434, 259, DIG. 127, 638, 651; 604/4, 5, 6

[56] References Cited

U.S. PATENT DOCUMENTS 3,228,877  1/1966  Mahon ........................... 210/651 X
4,350,156  9/1982  Malchesky et al. ............. 210/434 X

FOREIGN PATENT DOCUMENTS 2559154  7/1977  Fed. Rep. of Germany ...... 210/315
3004990  1/1982  Fed. Rep. of Germany ...... 210/315
 118895  3/1977  Japan .................................. 210/434

Primary Examiner—Frank Spear
Attorney, Agent, or Firm—Michael J. Striker

[57] ABSTRACT

An extracorporal removal from blood of toxins connected with albumen includes separating a blood plasma from cellular components, mixing a solution of low-molecular split reagents with the separated blood plasma with a dwell time of substantially between several seconds and 30 minutes in dependence upon the particular reagent, treating the thus treated blood plasma in an artificial kidney, and uniting the thus obtained plasma with the separated cellular components.

26 Claims, 2 Drawing Figures

METHOD OF AND ARRANGEMENT FOR EXTRACORPORAL REMOVAL OF TOXINS FROM BLOOD

BACKGROUND OF THE INVENTION

The present invention relates to a method of and an arrangement for extracorporal removal of toxins connected with albumin bodies from blood.

Toxins entering the body, whether they are waste products of metabolism or poisonous substances received with food or as medicaments, are in many cases connected with albumin bodies in the bloodstream and transformed in the liver to urineconnected substances which then are separated in the kidneys. There are cases in which this natural detoxicating mechanism in the liver fails and therefore the toxins are so enriched that the natural transport and buffer system of the blood albumin is overcharged and the physiologically untreated high concentrations of free toxins will then exist in blood. This very often happens in the event of acute possoning with sleeping medications, in the event of shock temporary liver failure in comatose condition, or in the event of chronic liver damage. It is therefore necessary to provide a method which makes possible removal extracorporally of such albumin-connected toxins without damaging the remaining substances contained in blood plasma. Methods of this type are known in the art. They are used for separating of toxins and operate in general in combination with adsorption means. A method of hemoperfusion should be mentioned in accordance with which blood is supplied through an adsorbent layer and then toxins are taken from the adsorbent. This method is little specific and does not lead, particularly in the event of toxins connected with albumin bodies, to the desired results.

German Offenlegungsschrifte Nos. 2,559,154 and 3,004,990 disclose methods and arrangements in accordance with which the adsorbents are first treated with aggregation inhibitors and embedded in or behind a membrane. Moreover, split reagents are introduced which split the bonds between toxins and albumin bodies. Thereby splitting of the toxins connected with the albumen bodies is carried out. Because of simultaneously occurring equilibrium adjustments between split reagents, albuminconnected toxins and split toxins and during the adsorption on the adsorbents the effectiveness is low, and both split reagents and toxins remain in a certain quantity in the blood.

SUMMARY OF THE INVENTION

Accordingly, it is an object of the present invention to provide a method of and an arrangement for extracorporal removal of toxins connected with albumin bodies from blood, which have high effectiveness, provide for removal of poisonous substances in high quantity, and involve no problems with handling.

In keeping with these objects, and with others which will become apparent hereinafter, one feature of the present invention resides, briefly stated, in a method in accordance with which blood plasma is separated in a first step from cellular components, a solution of low-molecular split reagents is admixed to the blood plasma in a second step, and after a dwell time of between several seconds and 30 minutes, depending upon the particular split reagents, the thus treated blood plasma is subjected to treatment in an artificial kidney in a third step, whereupon the obtained plasma is united with the separated cellular components.

In accordance with another feature of the present invention, which is advantageous for separating the cellular components, the blood plasma is separated from the cellular components by centrifuging. The centrifuging has, however, the disadvantage that there is a danger that the cellular components can be damaged by high mechanical action.

This disadvantage is eliminated in accordance with another advantageous feature of the present invention, wherein the separation of the cellular components can be carried out by microfiltration.

A very important feature of the invention is that the blood plasma is mixed with a solution of low-molecular split reagents. Such low-molecular split reagents are known. For example, they can be acetylsalicylic acid, acetylaminophenol, p-aminosalicylic acid, acetylcysteine, cysteine, fatty acids with 10-18 C-atoms, and also urea with sufficiently high concentration. The reaction time required for the splitting reaction is in many cases, particularly when the split reagents are used in high concentrations, equal to 2 seconds dwell time for a practically complete splitting.

For the fast-flowing splitting reaction, the mixing of the split reagent solution is advantageously performed with formation of turbulence in the flow of blood plasma.

The split reagents are used, advantageously, in a concentration of 1 mmol/l to 1 mol/l in buffered physiological saline solution.

For a fast split reaction, it is required that mixing of the plasma and the split reagent solution is performed with a maximum possible concentration of the split reagents. For this purpose it is advantageous when the solution of the split reagent is mixed with the blood plasma in a weight ratio of 1:100 to 2:1.

The split reaction proceeds in such a manner that the toxins in their low-molecular form with molecular weights of generally less than 1,000 are present in plasma and thereby not converted to the conventional urea-connected substance. However, they become separated in correspondence with the urea-connected substances, inside the artificial kidney. Since, moreover, the split reagents are low-molecular and also separated in the artificial kidney, this low-molecular split reagents and the lowmolecular toxins are separated in a subsequent step by treatment in an artificial kidney.

In accordance with an advantageous feature of the present invention, the treatment in the artificial kidney is carried out as a dialysis.

In accordance with a different embodiment of the invention, the treatment in an artificial kidney is carried out as a filtration. It should be considered that, in the event of utilization of the dialysis principle, different substances to be dialyzed are separated in correspondence with their concentrations and their molecule size, whereas in the event of filtration to the exclusion limit the molecules can be separated uniformly in correspondence with their concentration. In this case, the solution additionally loses filtration water which must be compensated prior to or after this. In the cases where substances with low molecular weight are present in high concentrations, the dialysis can be used, whereas in the event of high content of substances with high molecular weight the filtration possesses considerable advantages.

It is especially advantageous to combine both methods in one artificial kidney, when first the plasma solution is subjected to dialysis, and thereafter is subjected to filtration, or vice versa. In accordance with a preferred embodiment of the invention, the treatment in an artificial kidney is performed as a combination of dialysis and filtration.

It is especially important to completely carry out the separation of the toxins and the split reagents during treatment in the artificial kidney. In accordance with a further feature of the present invention, the treatment for this purpose is performed in several dialysis and/or filtration units arranged one after the other.

An additional advantageous feature of the treatment in an artificial kidney is that the blood plasma leaving the artificial kidney is partially returned to the artificial kidney, and during a further cycle is subjected to dialysis and/or filtration. The pure plasma leaving the artificial kidney is united with the separated cellular components to form a high quality blood. Thereby the invention makes possible recovery of blood released from toxins, which is suitable first of all for reinfusion for the same patient.

An arrangement for extracorporal removal from blood of toxins connected with albumin bodies has plasma separating means arranged to separate blood plasma from cellular components, mixing means arranged for receiving the separated blood plasma and mixing a low-molecular split reagent with the same with a dwell time of substantially between several seconds and 30 minutes, an artificial kidney arranged to receive the thus treated plasma and to treat the latter, and means for uniting the thus obtained plasma with the separated cellular components.

The above mentioned means may be connected by connecting conduits so that a first connecting conduit leads to a blood inlet opening of the plasma separating means, a second connecting conduit leads from a plasma outlet opening of the separating means to the mixing means, a third connecting conduit leads from the mixing means to the artificial kidney, a fourth connecting conduit leads from the artificial kidney to a blood discharge conduit, and a fifth connecting conduit leads from the blood outlet opening of the plasma separating means to the blood discharge conduit. Thus, the first connecting conduit is a blood conduit, the second connecting conduit is a plasma conduit, the third connecting conduit is a mixture conduit, the fourth connecting conduit is a pure plasma conduit, and the fifth connecting conduit is a thick blood conduit.

For fine treatment of blood, its feeding through the inventive arrangement is performed, advantageously, by natural fall, in that the blood is supplied from a highly located receiving container to the arrangement, and or in that the above mentioned means are arranged under one another or at different levels. It is also possible, alternatively or additionally, to provide a feeding device. Conventional blood pumps or corresponding devices which are utilized for other methods and arrangements for supplying blood for other purposes through closed conduits can be used as the feeding device. The output of such a device lies, for example, in the range of 1 ml/min to 500 ml/min.

Plasma separating means may be advantageously formed by known plasma centrifuges or plasma filters, wherein plasma filters have the advantage that, compared with plasma centrifuges, they work without moving parts and guarantee fine treatment of blood. Moreover, the plasma filter provides for continuous movement. Sometimes it is advantageous to arrange a plasma centrifuge and a plasma filter one behind the other, and particularly the centrifuge after the filter. The mixing means for mixing the split reagent to the blood plasma can be formed, for example, as a closed stirring container. For avoiding moving parts, it is also possible for the same purpose to use a mixing nozzle working with injector action. Frequently it suffices, however, to use a T-shaped or Y-shaped pipe in which both components to be mixed are supplied. For improved mixing in the event of utilization of the above mentioned mixing pipe, it can be advantageous to provide after the mixing pipe a mixing line in which sometimes not sufficiently mixed mixture is subjected to strong turbulence. In some cases, it is advantageous to use the above mentioned mixing devices or other not described devices in combination with one another, for example one after the other.

In dependence upon the desired split reaction provided by the split reagent in blood plasma, a longer reaction time can be required prior to treating of the blood plasma in the artificial kidney. For this purpose, either the diameter and/or the length of the mixing conduit leading from the mixing means to the artificial kidney can be selected so that the mixture of the blood plasma and the split reagent has a sufficiently long dwell time corresponding to the required reaction time in this conduit. Instead of this, between the mixing means and the artificial kidney a buffer container with sufficient dimensions can be provided for the same purpose.

The artificial kidney can be formed, in accordance with the invention, as a known dialysis device or also as a known filter. In some case, it is advantageous when both a dialysis device and a filter are arranged together and so that these devices are connected one after the other or in series. Moreover, it can be advantageous, during utilization of one of the two above mentioned types, to arrange several units in series connection.

With the utilization of a diafilter, it is advantageous to mix with the blood plasma as replacement for the liquid separated during filtration, a corresponding quantity of a physiological saline solution. This admixture of the physiological saline solution can be carried out prior to or after the filtration. In the present invention, it has been recognized as advantageous to mix the physiological saline solution with the blood plasma prior to the filtration. Advantageously, the same mixing device as used for admixing the split reagent can be used here. The physiological saline solution and the split reagent are mixed with one another before, i.e. before their admixture to the plasma. For this case, in accordance with a further feature of the present invention, auxiliary mixing means is provided which can correspond in its construction and operation to the above mentioned mixing means.

When it is required to return back to the artificial kidney a part of the blood plasma leaving the latter, a recirculation conduit can branch from the pure plasma conduit after the artificial kidney and open prior to the latter in the above mentioned part of the arrangement, advantageously into the mixture conduit. A correspondingly dimensioned feeding device, such as a pump, is arranged in the recirculating conduit to provide for a recirculating flow.

It is to be understood that the inventive arrangement is also provided with required measuring and control means, as well as with valves and the like whose detailed description is dispensed with, since these members are known and can be used by a skilled person in the art at suitable locations.

The same is true with respect to the mixing means and auxiliary mixing means, in which care must be taken to continuously dose the split reagent to the blood plasma in a predetermined quantity. Conventional dosing devices such as dosing pumps, apertured partitions, fine control valves, etc., can be used here, so that their detailed description is believed to be unnecessary.

For microfiltration of the plasma for separation of the cellular components, membranes can be used such as described, for example, in German Offenlegungsschrifte Nos. 3,006,888, 3,026,718, 3,042,110.

Membranes for artificial kidneys are available both for the dialysis and for the diafiltration, of which membranes for regenerated cellulose are in the foreground. Several membranes which can be used in the present invention are disclosed, for example, in the German Offenlegungsschrifte Nos. 2,823,985, 2,842,935, 2,842,836, 2,842,957, 2842,958, 2,848,601, 2,856,123, 2,932,761, 3,021,943 or 3,049,247. Advantageously, these membranes are used in module form.

The novel features which are considered characteristic for the invention are set forth in particular in the appended claims. The invention itself, however, both as to its construction and its method of use, together with additional objects and advantages thereof, will be best understood from the following description of specific embodiments when read in connection with the accompanying drawing.

DESCRIPTION OF THE PREFERRED EMBODIMENTS

Figure 1:
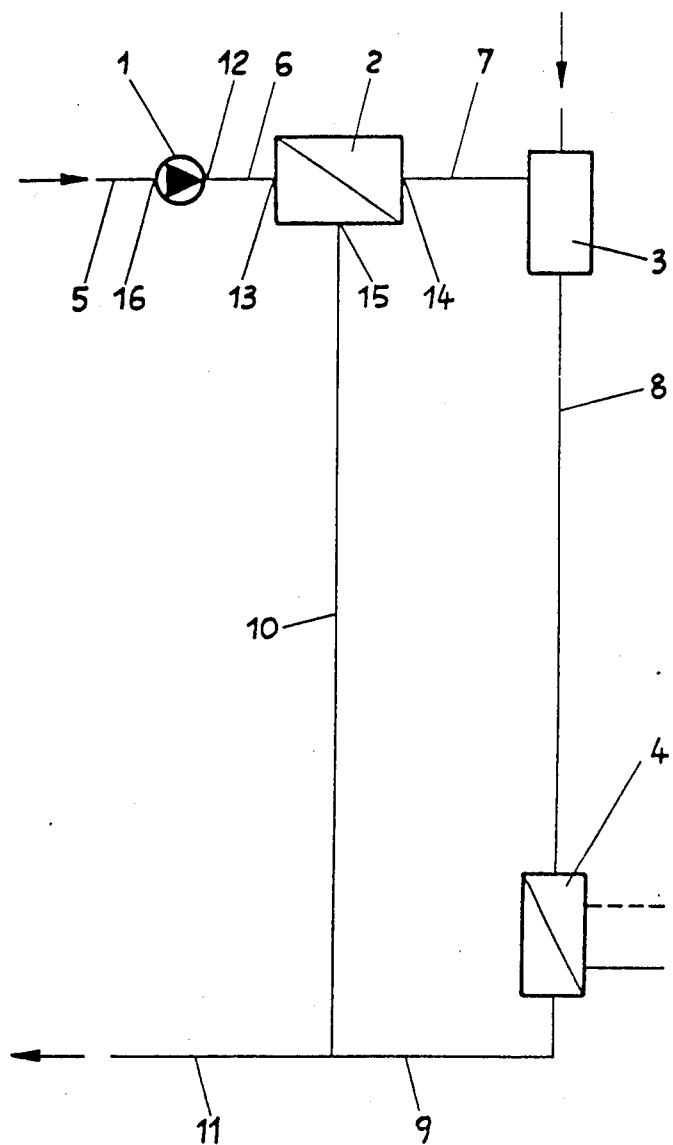
FIG. 1 is a view schematically showing an arrangement for extracorporal removal of toxins connected with albumin bodies from blood, in accordance with one embodiment of the present invention.

An arrangement in accordance with one embodiment of the present invention is shown in FIG. 1 and includes a feeding device (such as a pump) 1, a plasma separating device 2, a mixing device 3, and an artificial kidney 4.

The feeding device 1 is connected at its suction side 16 with a blood supplying conduit 5, and at its pressure side 12 with a first connecting conduit 6 (a blood conduit). The first connecting conduit 6 leads from the pressure side 12 of the feeding device 1 to a blood inlet opening 13 of the plasma separating device 2. A second conduit 7 (plasma conduit) leads from a plasma outlet opening 14 of the plasma separating device 2 to the mixing device 3. A third connecting conduit 8 (a mixture conduit) leads from the mixing device 3 to the artificial kidney 4. A fourth connecting conduit 9 (a clean plasma conduit) leads from the artificial kidney 4 to a blood discharge conduit 11. A fifth connecting conduit 10 (a thick blood conduit) opens in the blood discharging conduit 11 and is connected with a thick blood outlet opening 15 of the plasma separating device 2. At the point of the opening of the fifth connecting conduit 10 into the blood discharge conduit 11, the blood thickened in the plasma separating device 2 is again mixed with the detoxified blood plasma. The admixture of the reagent takes place in the mixing device 3.

Figure 2:
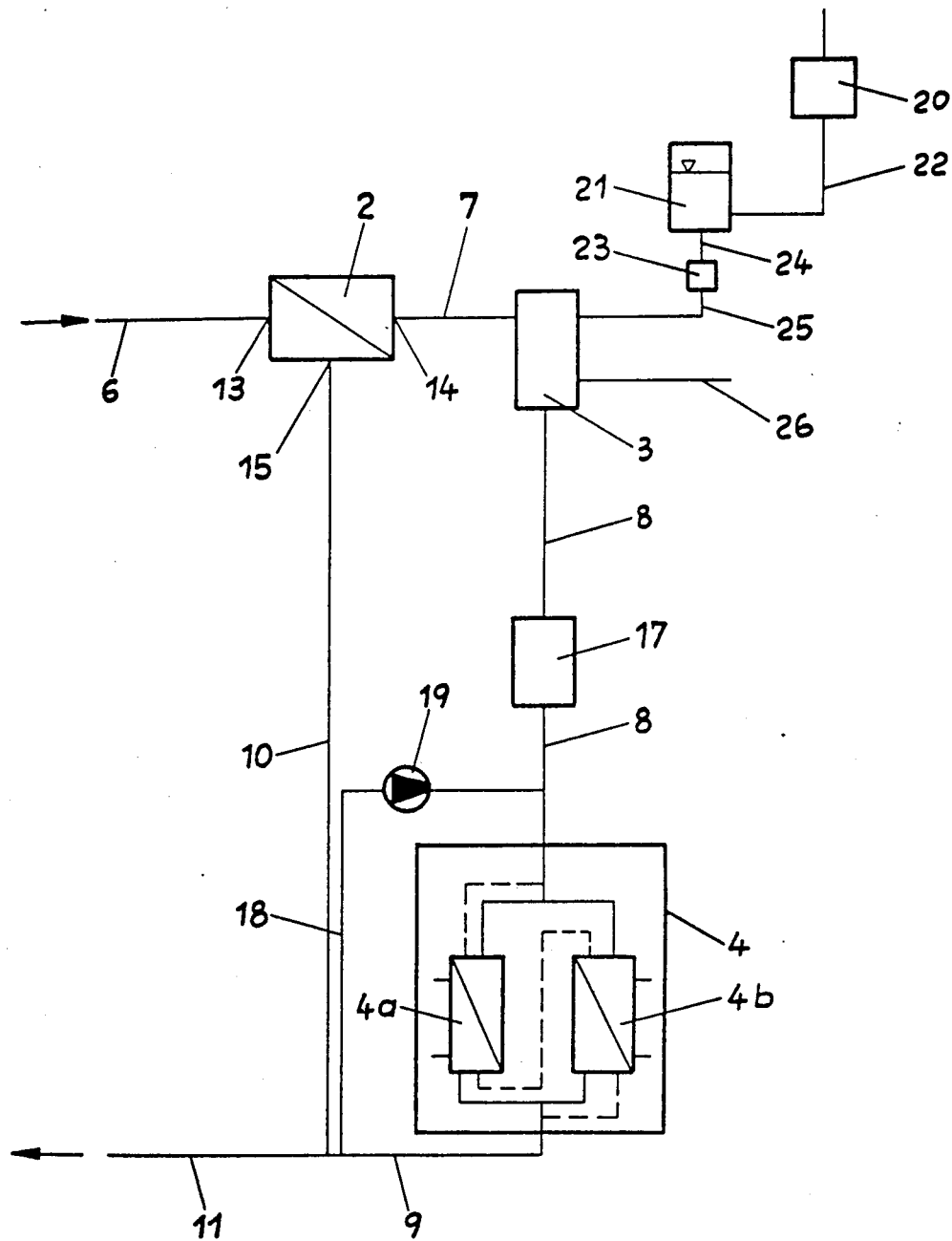
FIG. 2 is a view schematically showing an arrangement for extracorporal removal of toxins connected with albumin bodies from blood, in accordance with another embodiment of the invention.

The arrangement in accordance with a second embodiment shown in FIG. 2 has all the parts of the arrangement shown in FIG. 1. These parts are identified by the same reference numerals and perform the same functions described with respect to the embodiment of FIG. 1. In addition, the arrangement of FIG. 2 is provided with some auxiliary devices. This arrangement has an auxiliary mixing device 20 with which splitting reagents can be dissolved in a suitable solvent prior to the admixture to the blood plasma. The arrangement also has a supply container 21 which is connected via the pipe 22 with the auxiliary mixing device 20. The supply container 21 serves as a receiver for a dosing device 23 with which it is connected via a pipe 24. From the dosing device 23, a further pipe 25 leads to the mixing device 3. A further connection 26 leads to the mixing device 3, so that through the connection 26 the blood plasma, for example a physiological saline solution, can be admixed.

A surge chamber 17 is provided between the mixing device 3 and the artificial kidney 4 and increases the dwell time of the mixture of blood plasma and split reagents (and sometimes physiological saline solution) prior to the treatment in the artificial kidney 4. The artificial kidney 4 is composed in this embodiment of two units 4a and 4b, such as for example two dialysis devices or two diafilter devices, or one dialysis device and one diafilter device. It can also be composed of several such devices provided in any number. A parallel throughflow through both devices 4a and 4b is provided via pipes shown in solid lines. A throughflow in series after one another of both units 4a and 4b is provided by pipes shown in broken lines. This type of connection can also be provided when more than two units are utilized, with the aid of the respective pipes. A recirculating conduit 18 branches behind the artificial kidney 4 and opens prior to the artificial kidney 4 into the third connecting conduit 8. A feeding device 19 is arranged in the recirculating conduit 18 to provide a recirculating flow. With appropriate dimensioning of the recirculating device 19, a recirculating flow of any height can be produced, which can be adjusted by respective control organs to the desired value.

With the utilization of a plasma centrifuge, purification of the cellular components with the disinfected blood plasma takes place by digesting, so that the fifth connecting conduit (thick blood conduit) can in FIGS. 1 and 2 be dispensed with.

It will be understood that each of the elements described above, or two or more together, may also find a useful application in other types of constructions differing from the types described above.

While the invention has been illustrated and described as embodied in an arrangement for extracorporal removal from blood of toxins connected with albumen bodies, it is not intended to be limited to the details shown, since various modifications and structural changes may be made without departing in any way from the spirit of the present invention.

I claim:

1. A method of extracorporal removal from blood of toxins connected with albumin bodies, comprising the steps of
    withdrawing blood from a patient;
    separating a blood plasma of the withdrawn blood from cellular components;
    mixing a solution of a low-molecular split reagent with the separated blood plasma with a dwell time of substantially between several seconds and 30 minutes in dependence upon a particular reagent;

treating the thus mixed blood plasma with the low-molecular split reagent in an artificial kidney so as to separate toxins with molecular weight substantially less than 1,000 and the low-molecular split reagent from the plasma; and uniting the thus obtained plasma with the separated cellular components.

2. A method as defined in claim 1, wherein said separating step includes separating the blood plasma from the cellular components by centrifuging.

3. A method as defined in claim 1, wherein said separating step includes separating the blood plasma from the cellular components by microfiltration.

4. A method as defined in claim 1, wherein said mixing step includes mixing the solution of low-molecular split reagent with the separated blood plasma with formation of a turbulence in a stream of the blood plasma.

5. A method as defined in claim 1, wherein said mixing step includes using of the low-molecular split reagent which are dissolved with a concentration of substantially between 1 mmol/l and 1 mol/l, in dependence upon a particular reagent.

6. A method as defined in claim 1, wherein said mixing step includes using of the low-molecular split reagent which is dissolved in buffered physiological saline solution.

7. A method as defined in claim 1, wherein said mixing step includes mixing the low-molecular split reagent with the separated blood plasma in a weight ratio of between 1:100 and 2:1.

8. A method as defined in claim 1, wherein said treating step includes treating of the thus treated blood plasma in the artificial kidney by dialysis.

9. A method as defined in claim 1, wherein said treating step includes treating of the thus treated blood plasma in the artificial kidney by filtration.

10. A method as defined in claim 1, wherein said treating step includes treating of the thus treated blood plasma in the artificial kidney by a combination of dialysis and filtration.

11. A method as defined in claim 1, wherein said treating step includes treating of the thus treated blood plasma in the artificial kidney in several units arranged one behind the other and performing at least one of dialysis and filtration.

12. A method as defined in claim 1, wherein said treating step includes treating of the thus treated blood plasma in the artificial kidney in several dialysis and filtration units arranged one behind the other.

13. A method as defined in claim 1; and further comprising the step of returning the plasma after leaving the artificial kidney, partially back into the artificial kidney.

14. An arrangement for extracorporal removal from blood of toxins connected with albumin bodies, comprising plasma separating means arranged to separate a blood plasma of blood withdrawn from a patient from cellular components;

mixing means arranged for receiving the separated blood plasma and mixing a low-molecular split reagent with the same with a dwell time of substantially between several seconds and 30 minutes, in dependence upon a particular reagent;

an artificial kidney arranged to receive the thus treated plasma and to treat the mixed blood plasma with the low-molecular split reagent so as to separate toxins with molecular weight substantially less than 1,000 and the low-molecular split reagent from the plasma; and means for uniting the thus obtained plasma with the separated cellular components.

15. An arrangement as defined in claim 14, wherein said plasma separating means has a blood inlet opening and plasma and blood outlet openings; and further comprising a plurality of conduits including a first connecting conduit leading to said blood inlet opening of said plasma separating means, a second connecting conduit leading from said plasma outlet opening of said separating means to said mixing means, a fourth connecting conduit leading from said mixing means to said artificial kidney, a blood discharge conduit, a third connecting conduit leading from said artificial kidney to said blood discharge conduit, and a fifth connecting conduit leading from said blood outlet opening of said plasma separating means to said blood discharge conduit so that said fourth and fifth connecting conduits together form said unit means.

16. An arrangement as defined in claim 14, wherein said plasma separating means for separating the blood plasma from the cellular components is formed as a plasma centrifuge.

17. An arrangement as defined in claim 14, wherein said plasma separating means for separating the blood plasma from the cellular components is formed as a plasma filter.

18. An arrangement as defined in claim 17, wherein said plasma filter of said plasma separating means for separating the blood plasma from the cellular components is formed as a microfilter.

19. An arrangement as defined in claim 14, wherein said mixing means for mixing the separated blood plasma with the low-molecular split reagent is formed as a closed stirring container.

20. An arrangement as defined in claim 14, wherein said mixing means for mixing the separated blood plasma with the low-molecular split reagent is formed as a mixing nozzle which operates with an injection action.

21. An arrangement as defined in claim 14, wherein said artificial kidney for treating the blood plasma is formed as at least one dialysis device.

22. An arrangement as defined in claim 14, wherein said artificial kidney for treating the blood plasma is formed as at least one filter.

23. An arrangement as defined in claim 14, wherein said artificial kidney for treating the blood plasma includes at least one dialysis device and at least one filter.

24. An arrangement as defined in claim 14; and further comprising a buffer chamber provided between said mixing means and said artificial kidney to increase the dwell time.

25. An arrangement as defined in claim 15; and further comprising a recirculating conduit which branches after said artificial kidney from said fourth conduit and opens prior to said artificial kidney to a plasma stream, and feeding means arranged to feed a recirculation stream through said recirculating conduit.

26. An arrangement as defined in claim 14; and further comprising auxiliary mixing means arranged for producing a solution of the split reagents and a respective solvent, and supplying the same into said first-mentioned mixing means.

* * * * *